United States Patent [19]

Monzen

[11] Patent Number: 4,664,682
[45] Date of Patent: May 12, 1987

[54] DEVICE FOR RECEIVING AND TREATING BLOOD

[75] Inventor: Takashi Monzen, Tama, Japan

[73] Assignee: Terumo Kabushiki Kaisha trading as Terumo Corporation, Tokyo, Japan

[21] Appl. No.: 888,627

[22] Filed: Jul. 21, 1986

Related U.S. Application Data

[63] Continuation of Ser. No. 658,882, Oct. 9, 1984, abandoned.

[30] Foreign Application Priority Data

Nov. 11, 1983 [JP] Japan .................. 58-211926
Nov. 11, 1983 [JP] Japan .................. 58-211927
Aug. 7, 1984 [JP] Japan .................. 59-165453

[51] Int. Cl.⁴ ............................................ B01D 19/02
[52] U.S. Cl. ........................................... 55/178; 55/87; 128/DIG. 3; 210/436; 210/188; 604/126; 604/406
[58] Field of Search .................. 55/87, 159, 178; 128/DIG. 3; 210/188, 436, 472, 927; 604/4–6, 126, 400

[56] References Cited

U.S. PATENT DOCUMENTS

| | | | |
|---|---|---|---|
| 3,507,395 | 4/1970 | Bentley | 210/443 |
| 3,701,433 | 10/1972 | Krakauer et al. | 210/430 |
| 3,827,562 | 8/1974 | Esmond | 210/304 |
| 3,993,067 | 11/1976 | Schachet et al. | 128/214 C |
| 4,054,523 | 10/1977 | Ingenito et al. | 210/188 |
| 4,059,108 | 11/1977 | Latham | 604/6 |
| 4,164,468 | 8/1979 | Raible | 210/646 |
| 4,205,042 | 5/1980 | Lobdell et al. | 55/178 X |
| 4,208,193 | 6/1980 | Munsch et al. | 55/36 |
| 4,282,180 | 8/1981 | Raible | 128/DIG. 3 |
| 4,344,777 | 8/1982 | Siposs | 55/178 |

Primary Examiner—Charles Hart
Attorney, Agent, or Firm—Frishauf, Holtz, Goodman & Woodward

[57] ABSTRACT

In a blood reservoir comprising a hollow housing and filtration/defoaming and blood collecting sections therein; the blood collecting section is located below and separated from the filtration/defoaming section receiving bubbled blood and has a sufficient capacity, typically 500 to 2,500 ml, to keep blood collected therein out of contact with the filtration/defoaming section; guide means in the form of a cone-shaped deflector is disposed between the filtration/defoaming section and the base of the housing to lead along its inner surface defoamed blood from the filtration/defoaming section to the collecting section without dripping. The filtration/defoaming section includes a concentric assembly of a pleated filter, a tubular member inwardly spaced apart from the filter to define a blood channel inside and to define a space outside for allowing bubbles to separate from the blood, a defoaming member about the filter, and a cylindrical distributor member inside the filter and extending through the tubular member, the tubular member protecting the upper portion of the filter from being wetted with blood.

39 Claims, 14 Drawing Figures

DEVICE FOR RECEIVING AND TREATING BLOOD

This application is a continuation of application Ser. No. 658,882, filed Oct. 9, 1984, now abandoned.

BACKGROUND OF THE INVENTION

The present invention relates to a device for receiving and treating blood, and more particularly, to a cardiotomy reservoir used in oxygenator circuits employed for extracorporeal circulation during open-heart surgery.

FIG. 1 shows a typical oxygenator circuit. Blood drained from the patient's vena cava passes through a venous drainage line 1, and blood from the surgical field passes from aspiration lines 2 and pumps 3 through a cardiotomy reservoir 4 and a line 5, before both entering a venous reservoir 7 held in a volume-regulating means 6. The blood is then sent by a pump 8 to an oxygenator 9 with a heat exchanger where it is oxygenated. The blood is then returned to the patient's body via an arterial infusion line 10.

Today, in addition to the defoaming and collection of blood aspirated from the surgical field, be this the thoracic cavity, cardiac cavity or another area, a great many cardiotomy reservoirs now in use have been provided also with a filter that removes foreign matter, such as tissue and microaggregates, which is sucked off together with blood from the operating field or is present in trasfusing blood. Such cardiotomy reservoirs thus have three important functions: filtration, defoaming, and blood collection. A number of problems have been identified with each of these functions in cardiotomy reservoirs in use today.

(1) Problems with filtration

When blood containing large amounts of foreign matter such as tissue and microaggregates is passed through the filter, premature clogging of the pores often arises before full use can be made of the filter. In the case of pleated filters, the filter is arranged cicumferentially, leaving an inner cavity in which blood pools. This makes it difficult to correctly determine the amount of blood within the reservoir. The blood quantity indicated by the scale on the reservoir housing thus differs from the actual amount of blood in the reservoir, making it impossible to get a true reading when necessary. Another problem is that good filter performance conflicts with the rapid separation of microbubbles from blood within the filter; getting a good balance of both properties is quite difficult.

(2) Problems with defoaming

Blood entering the cardiotomy reservoir is filtered and defoamed by a filter and defoaming agent before it is collected in the housing. However, in constructions where blood or priming fluid draining from the filter/defoamer drips directly onto the surface of defoamed blood pooled in the reservoir, bubbles can form again. Returning of blood containing microbubbles to the patient may possibly induce cerebropathy due to capillary occlusion or other complications.

To avoid such problems, some cardiotomy reservoirs are constructed with the filter/defoamer in contact with the base of the housing. However, this type of reservoir tends to give rise to "air blockage", meaning the trapping of air bubbles within the blood outlet port at the base of the housing and the tubing connected to this port. In an oxygenator circuit utilizing a membrane-type oxygenator and a closed venous reservoir, this presents a large danger of air entry into the venous reservoir, oxygenator, and patient. "Air blockage" here refers to the trapping of air within the tubing connected to the blood outlet port during a large influx of blood into the reservoir while the tubing is clamped off at the blood level in the tubing.

As for cardiotomy reservoirs having a filter built therein, the greater resistance of high-performance filters in use recently has made functionally imperative a construcion that defoams following filtration. Forced filtration under positive pressure occurs in filtering the incoming air-containing blood. However, with positive filtration, as the blood flow rate rises, the capacity of the defoamer to treat blood is at some point exceeded, and the air under pressure causes blood to spurt from the filter. Bubbles reform in the blood, which hampers subsequent defoaming operations. This is accompanied also by a large pressure rise in the filter, which tends to diminish filter performance. Attempts have been made to get around this problem by employing a cyclone-type air separation structure at the blood inlet port. However, such a setup is unable to cope with the influx of large volumes of air and invites a pressure rise, resulting in very poor defoaming performance.

(3) Problems with blood collection

The shape and structure of the housing also poses problems in terms of blood collection within the reservoir. Mold fabrication for a housing made of two flanged halves bonded at the center is easy. However, with this type of construction, in addition to the possibility of blood leaking from the junction, the calibration of volumetric graduations on labels is difficult, which tends to invite inaccurate calibration of the collected blood volume near the junction. Moreover, in some particular open-heart cases, blood volume measurements are ofter taken via a vent line to check for circulatory abnormalities and valvular incompetence. The heart is in an ischemic state. When pulmonary vein circulation is abnormal, blood pools in the left ventricle. The degree of abnormality can be determined by the amount of this pooled blood. The existence of valvular incompetence in the vena cava can also be determined by the amount of pooled blood in the left ventricle. A scale with fine graduations is required for the measurement of these volumes through a vent line. For this reason, users desire the base of the housing and the blood outlet port to be shaped such as to allow easy blood volume read-out.

Another consideration is blood and bubble separation. Among filters having the same surface area, a longer filter provides better separation. Hence, long filters reaching almost to the base of the housing are often used. However, in cardiotomy reservoirs of this type, the blood remains in extended contact with the filter material, resulting in significant complement activation and silicone extraction, both problems being of increased concern lately. Typical examples of cardiotomy reservoirs in which the filter extends down to the vicinity of the housing base are disclosed in U.S. Pat. Nos. 4,164,468 and 4,209,193.

SUMMARY OF THE INVENTION

It is, therefore, an object of the present invention to provide a blood receiving and treating device of the type often referred to as a cardiotomy reservoir having separate filtration/defoaming and blood collecting sections that limits the period during which the blood comes in contact with the substances of the filtration/defoaming section to just the time it takes for the blood to pass through the filter.

Another object of the present invention is to provide a blood reservoir having separate filtration/defoaming and blood collecting sections that allows easy verification of the amount of blood collected in the blood collecting section so that the amount of blood returned can be accurately determined.

A further object of the present invention is to provide a blood reservoir having an improved filter assembly capable of fast separation of bubbles from blood for a prolonged period of time.

A still further object of the present invention is to provide a blood reservoir having an improved filter assembly ensuring continuous escape of air of bubbles separated from blood.

An additional object of the present invention is to provide a blood reservoir having separate filtration/defoaming and collecting sections and guide means interconnecting these sections for blood communication wherein once blood is defoamed in the filtration/defoaming section, air bubbles will never be created in the blood during its transfer therefrom to the collecting section.

According to a first aspect of the present invention, there is provided a device for receiving and treating blood comprising a hollow housing having inlet means opened at the housing top for introducing blood into the housing and an outlet opened at the housing base for discharging blood out of the housing. An upper filtration/defoaming section is disposed in the housing for filtering and defoaming blood from the inlet means. A lower blood collecting section is defined in the housing adjacent its base for collecting blood such that the blood in said collecting section discharges out of the housing through the outlet. Guide means extends between the filtration/defoaming section and the housing base and is shaped to converge from the filtration/defoaming section toward the center of the housing base and including a convergent inner surface for continuously leading blood that has been filtered and defoamed in the filtration/defoaming section to the housing base along the inner surface without dripping.

In one preferred embodiment of the present invention, the filtration/defoaming section is a filter/defoamer assembly of cylindrical configuration, and the guide means comprises a cone-shaped deflector having a divergent open end in engagement with the lower edge of the filter/defoamer assembly and a convergent open end in engagement with the base of the housing for fluid communication.

In a further preferred embodiment, a delivery extremity of the filter/defoamer assembly at which blood is delivered therefrom to the deflector is spaced apart from that portion of the inner surface of the deflector that receives blood from the filter/defoamer assembly at a distance equal to or slightly less than the vertical dimension of a blood droplet hanging from the delivery extremity.

The guide means further comprises means for defining a plurality of blood flow channels on the inner surface of the cone-shaped deflector. A plurality of radial fins extend the entire length of the deflector to define the channels.

According to a second aspect of the present invention, there is provided a device for receiving and treating blood comprising a hollow housing having inlet means opened at the housing top for introducing blood into the housing and an outlet opened at the housing base for discharging blood out of the housing, and a filtration/defoaming section disposed in the housing to receive bubbled blood through the inlet means. The filtration/defoaming section includes (a) a tubular filter, (b) a tubular member defining a blood channel in fluid communication with the blood inlet at the top and disposed inside the filter to extend a part of the axial length of the filter for protecting an upper portion of the filter from being wetted with blood, the tubular member being spaced apart from the filter to define a space for allowing bubbles to separate from the blood, and (c) a defoaming member disposed about the filter. The filtration/defoaming section further comprises a cylindrical distributing member disposed inside the filter and extending through the tubular member for distributing the blood coming from the inlet uniformly to the filter.

BRIEF DESCRIPTION OF THE DRAWINGS

The above and other objects, features, and advantages of the present invention will become more apparent by reading the following description taken in conjunction with the accompanying drawings, in which.

DESCRIPTION OF THE PREFERRED EMBODIMENTS

The device for receiving and treating blood is hereinafter referred to as a blood reservoir for the convenience of description. It should be noted that the blood reservoir disclosed herein is generally of the type referred to as a cardiotomy reservoir.

Figure 2:
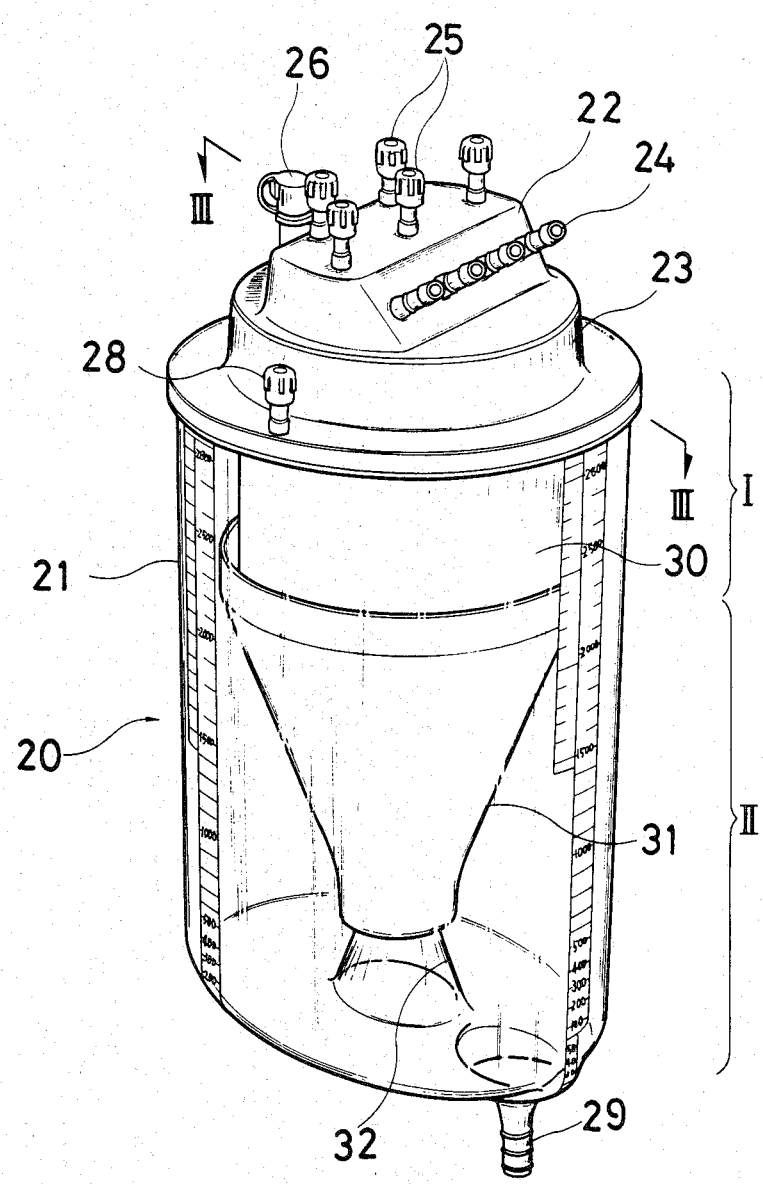
FIG. 2 is a perspective view of one preferred embodiment of the blood reservoir according to the present invention.
Figure 3:
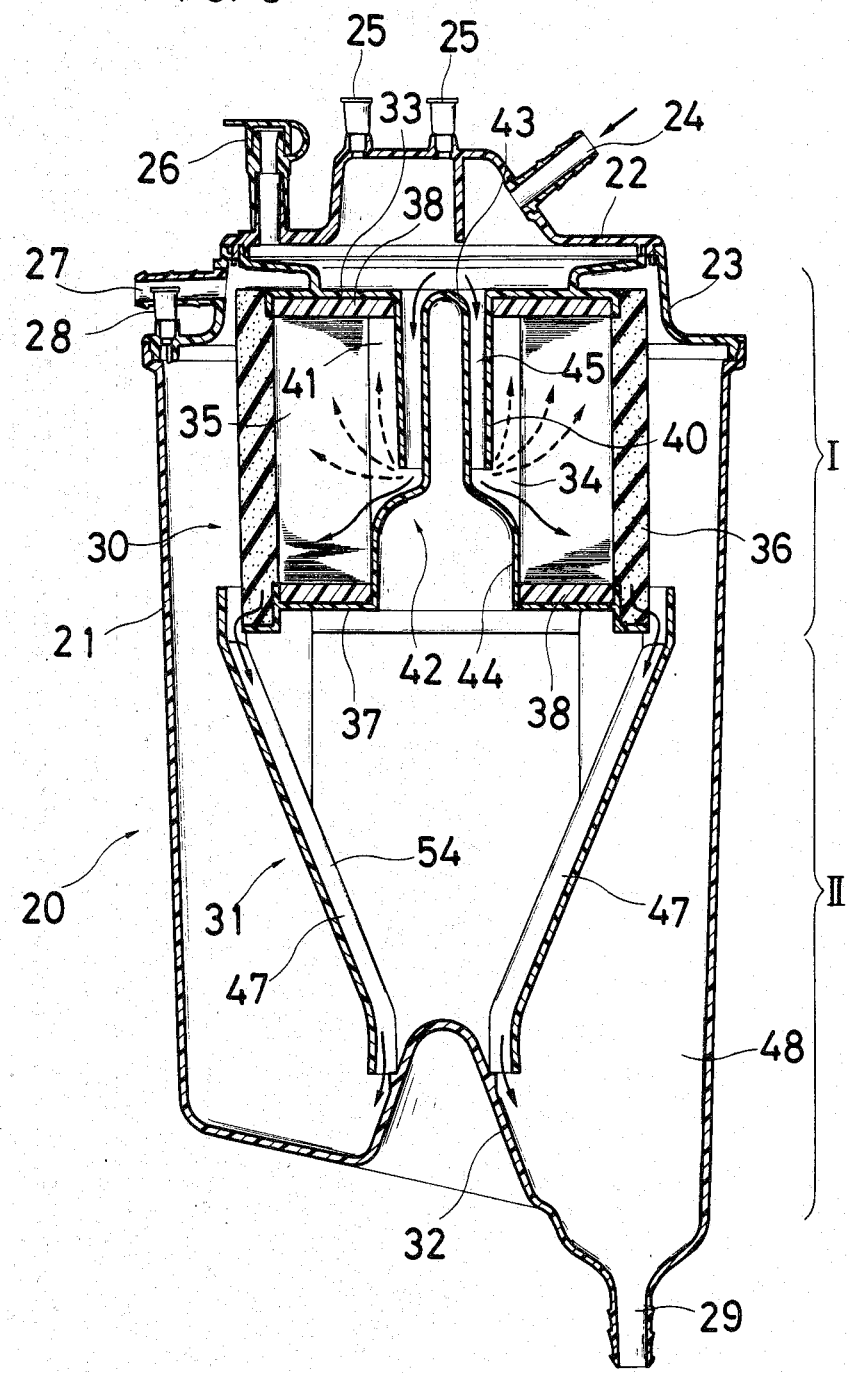
FIG. 3 is a vertical sectional view of the blood reservoir taken along lines III—III in FIG. 2.

FIG. 2 is a perspective view of a blood reservoir 20 according to one preferred embodiment of the present invention. FIG. 3 is a vertical sectional view of the same reservoir taken along lines III—III in FIG. 2. This blood reservoir 20 comprises a substantially cylindrical housing 21 in which a filtration/defoaming section I and a blood collecting section II are separately arranged. The housing 21 is a clear, hard structure made of a rigid plastic material such as polycarbonate, acrylonitrile-styrene copolymer, polyester, polyamide, polyvinyl chloride, and acrylonitrile-butadiene-styrene copolymer, and may preferably be molded as a one-piece member. The housing 21 at the top is provided with a cover assembly comprising first and second covers 22 and 23 which are rotatably mated with each other to allow for free connection of extracorporeal circulation lines. Aspirated blood inlet ports 24, filter-built-in infusion and transfusion ports 25, and a priming port 26 are provided on the first cover 22, and an air-venting port 27 and a filter-free infusion port 28 are provided on the second cover 23. The barrel of housing 21 is hollow and substantially cylindrical. The base of housing 21 is sloped towards an off-centered blood outlet port 29 and has formed at the center thereof a raised support 32 that bears a filter/defoamer assembly 30 and a cone-shaped deflector 31.

Although a two-piece housing has undeniable advantages in terms of ease of mold-making, a one-piece member construction (that does not include the top) without flanges or joints as required for joining two pieces is preferable for the housing 21 for leak-proofness, volumetric scale marking, label attachment and other purposes. The absence of bonded areas is particularly desirable at the base in order that blood does not pool at the base. The blood outlet port 29 is preferably off-centered or situated eccentrically near the periphery of the housing base because visual reading of scale and blood volume is otherwise difficult or inaccurate. Moreover, since it may be necessary in some open-heart surgery cases to know the precise amount of even small volumes of blood, the blood outlet port 29 may preferably be shaped as a smoothly curved funnel. Scale readings are especially easy to take when this port is given a rounded, typically hemispherical shape.

When blood passes to the venous reservoir through a tubing connected to the blood outlet port 29 having this type of smoothly curved funnel shape, the blood flows along the walls of blood outlet port 29 and the tubing, eliminating the "air blocking" phenomenon described earlier. "Air blocking" is similarly prevented even when the blood level rises above or falls below the blood outlet port on account perhaps of adjustments in the blood reservoir height to correct the amount of intracorporeal blood, which is continuously monitored, or fluctuations in the influx of blood from the surgical field.

The filter/defoamer assembly 30 situated in the upper part of housing 21 is supported, together with deflector 31 below it, between an upper support 33 extending from the first cover 22 and the raised support 32 on the housing base. The filter/defoamer assembly 30 includes a plurality of concentrically arranged functional elements. Air-containing blood directed into the center of filter/defoamer assembly 30 is first uniformly distributed and the blood and bubbles separated, following which the blood is filtered and defoamed. After being defoamed, the blood passes over deflector 31 to the bottom of the housing and collects in blood collecting section II without reforming microbubbles.

The filter/defoamer assembly 30 comprises a tubular filter 35 defining an inner cavity 34 and an annular defoamer 36 about the periphery thereof. The filter 35 is held in place by adhesive layers 38 between upper support 33 and a lower support 37. The defoamer 36 encloses the filter 35 and is retained by lower support 37. The cone-shaped deflector 31 is, in turn supported between lower support 37 and raised support 32. Upper support 33 has a cylindrical portion or barrier 40 extending straight down within inner cavity 34 in filter 35 to a length shorter than the axial length of the filter, preferably to substantially the midpoint of the axial length of the filter. Cylindrical barrier 40 and filter 35 defines therebetween an annular space 41. The presence of cylindrical barrier 40 prevents blood from entering directly into this space. As a result, that portion of the filter behind space 41 is not wetted, allowing air in the bubbles separated from the blood to pass through this portion, and be discharged from vent port 27 via filter 35 and defoamer 36.

The lower support 37 has a hollow distributor member 42 that extends upward through cavity 34 in filter 35. Hollow distributor member 42 includes a lower part 44 in abutment with the folds of filter 35 and an upper part 43 of a reduced diameter extending upward through barrier 40 to about the level of upper support 33. Hollow distributor member 42 and cylindrical barrier 40 may preferably be concentric with filter/defoamer assembly 30. A space 45 is defined between distributor member 42 and cylindrical portion 40 to form a blood channel. The head of distributor upper part 43 may be rounded such as to distribute the incoming blood evenly. The junction between the upper and lower parts of the distributor member is tapered for the same purpose.

In prior art blood reservoirs, a cavity is formed inside the filter without this blood-distributing hollow member. This creates a problem because an unmeasurable amount of blood can pool within the cavity. According to the present invention, hollow distributor member 42 is located within cavity 34 of filter 35 to a substantial distance, occupying a substantial portion of the cavity and eliminating an unnecessary space. This permits the even distribution of blood to filter 35 and effective utilization of the filter surface by virtue of the formation of blood/microbubble separation space 41 between cylindrical barrier 40 and filter 35. As a result, the channeling observed in conventional blood reservoirs does not arise. The hollow distributor member 42 may preferably be formed of a rigid plastic material that can confine the diameter of cavity 34 in filter 35, for example, polycarbonate, acrylonitrile-styrene copolymer, polyamide, polyester, polyvinyl chloride, acrylonitrile-butadiene-styrene copolymer, and polypropylene.

Figure 6A:
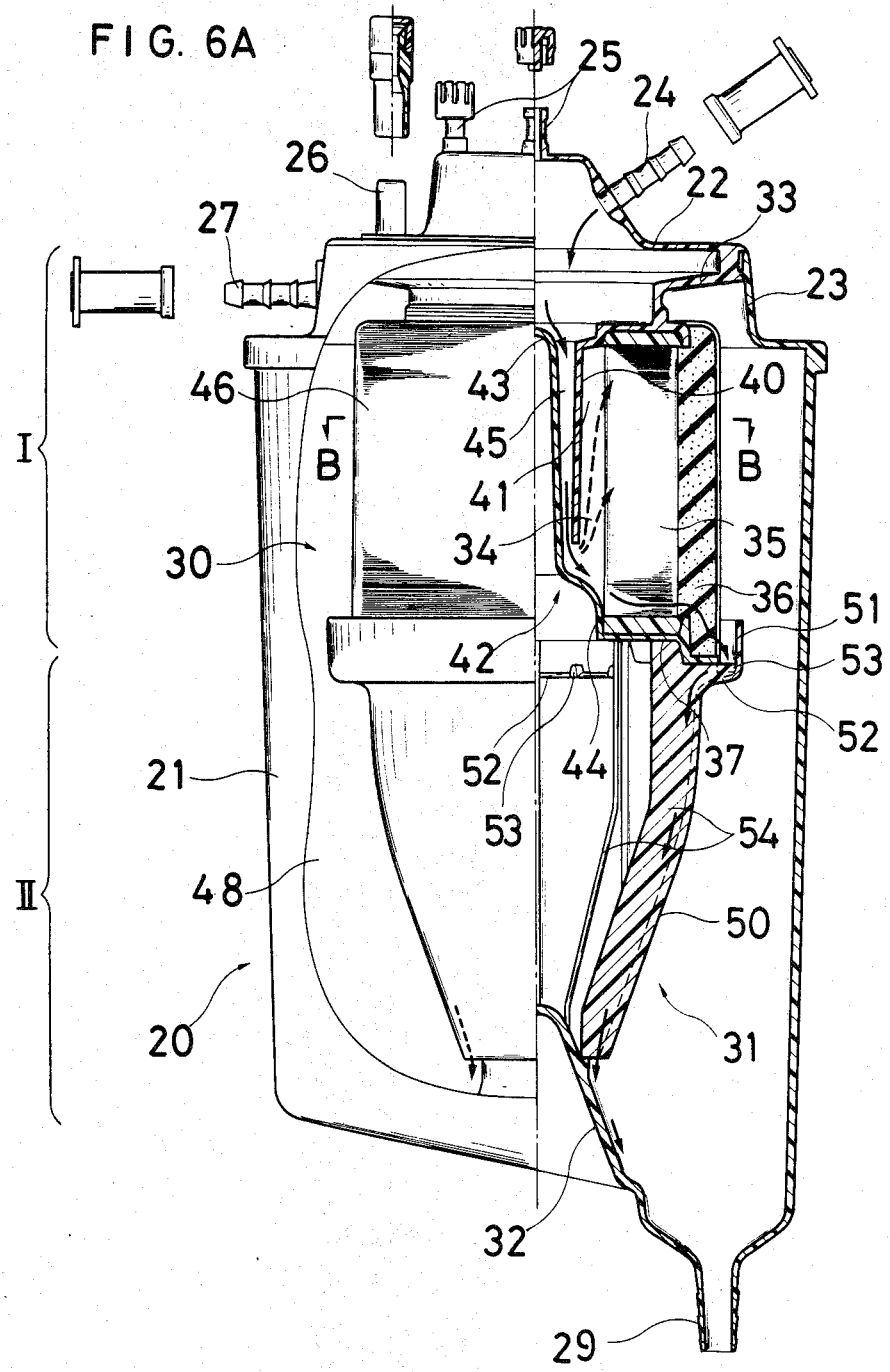
FIG. 6A is an elevational, partially cut-away, view of a further embodiment of the blood reservoir according to the present invention.
Figure 6B:
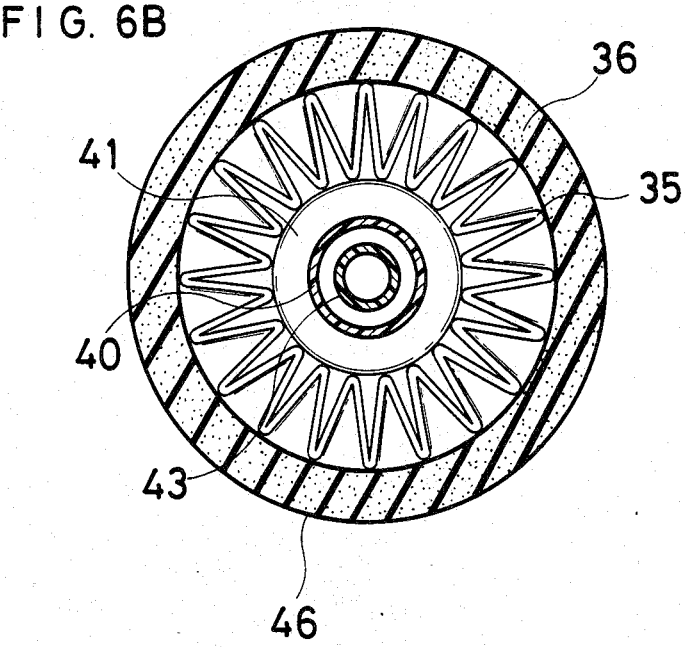
FIG. 6B is a cross section of the filter/defoamer assembly taken along lines B—B in FIG. 6A.

A variety of filters may be used as filter 35 which encircles distributor member 42. Whether the filter used is a screen-type filter with a pore size of about 20 microns or a depth-type filter that works by adsorption, it may desirably be in the form of a pleated filter for compactness and light weight as best shown in FIG. 6B. It is preferably a laminate filter including main filters sandwiched between support filters. Whether or not filter 35 is pleated, it may preferably be in contact with hollow distributor member 42 at regular intervals, while leaving spaces therebetween. This is desirable because the contact of filter 35 with hollow distributor member 42 at regular intervals increases the effective filter area. The spaces between filter 35 and hollow distributor member 42 provide for holding foreign matter, such as tissue and microaggregates, that interferes with the effective utilization of the filter by clogging the filter pores or causing channeling.

It has already been noted that blood reservoirs with an internal filter through which blood is filtered under positive pressure have the tendency that as the blood flow rate rises, the blood treatment capacity diminishes and blood spurts from the filter under the positive pressure. This causes microbubbles to form, which is undesirable for the subsequent debubbling process. To prevent microbubble reformation, the filter should be pretreated with a defoaming agent. It is generally desirable to use a defoaming silicone (such as silicone oil and silicone compound having silica added) as the defoaming agent, and a material such as nylon, polyester, and polypropylene as the filter material. The filter itself may be comprised of knitted and nonwoven fabrics of the above materials. The application of defoaming agent to the filter permits the bubbled blood to be separated into air and blood or fluid upon contact with the filter. This checks pressure rise across the filter and helps sustain the filtering capacity of the filter.

The function of defoamer 36 enclosing filter 35 is to defoam blood that has been filtered or filtered and defoamed by filter 35 upstream of the defoamer. Defoamer 36 may be formed from a material such as urethane foam, stainless steel ribbons, and polypropylene mesh having defoaming agents applied. The defoaming agents used herein may be any of the defoaming agents previously mentioned for the filter. Usually, a fabric cover 46, preferably a tricot bag encloses defoamer 36 as shown in FIGS. 6A and 6B.

The blood reservoir of the present invention is separated into filtering/defoaming section I and blood collecting section II. As noted earlier, the provision of separate sections avoids the immersion of filter 35 and defoamer 36 in collected blood that occurs in conventional blood reservoirs, thereby reducing contact of the blood with foreign matter as much as possible. This type of construction suppresses complement activation by materials used in the blood reservoir and the extraction of silicone, both problems that have prompted widespread concern recently. In addition, this blood reservoir reduces the dead volume of blood within filter 35 and defoamer 36, and provides graduated scales that allow the user to accurately determine the amount of blood returned to the patient. [For the sake of reference, complements are certain complements for proteins in serum that play a vital enzymatic role whenever an antigen-antibody reaction occurs in the body. Complement activation refers to the activation of these complements, which causes cell membrane disorders, disorders of the inflammation response and the body's host defense mechanisms against infection. Complements are used up or consumed by activation to temporarily lower the immunity of the body, increasing the risk of infection.]

In order to achieve these objects, the cone-shaped deflector 31 is provided at the bottom of filter/defoamer assembly 30 such as to lead the blood filtered and defoamed from filtration/defoaming section I to blood outlet port 29 at the base of housing 21 without the reemergence of microbubbles. Deflector 31 converges vertically downwards, that is, has a divergent open end at the top and a convergent open end at the bottom, and is supported on raised support 32 at the center of the housing base. As shown in FIG. 3, a plurality of guide fins 54 form trough-like channels 47 on the deflector inner surface. Deflector 31 may preferably be positioned such that it does not come in contact with, or the channels open up onto, the barrel of housing 21 or the housing base adjacent thereto. Should the deflector 31 and the housing contact in this manner, the point of contact may be easily mistaken as the blood level when the true blood level is lower than the point of contact, inviting an error by the surgeon. Moreover, because blood is continuously flowing over the convergent inner surface of the deflector, the deflector made of a clear material tends to make the correct blood level difficult to ascertain. Hence, the deflector should preferably be made of a material that is opaque or does not suggest the color of blood. The defoamed blood that leaves filter/defoamer assembly 30 passes over the trough-like channels 47 on deflector 31, forming gently moving streams that cause little disruption of the collected blood and do not give rise to microbubble formation.

Because a blood volume of about 300 to 500 ml is required at all times within a sealed system, blood collecting section II which does not contact filtration/defoaming section I should have a blood collecting capacity of at least 500 ml. When the aorta is cross-clamped during surgery, cardioplegia coolant is refluxed to provide myocardial protection. Since over 2000 ml of cardioplegia coolant may sometimes be required for this purpose, the capacity of the reservoir should have an upper limit of about 2,500 ml.

Deflector 31 guides blood that has been filtered and defoamed down to the base of hollow housing 21 without reformation of microbubbles. Many conventional deflectors are constructed such that blood flows down along the upper surface thereof to the base of the housing. In such constructions, the blood on the deflector and the blood level in the blood collecting section are often easily confused.

Figure 4:
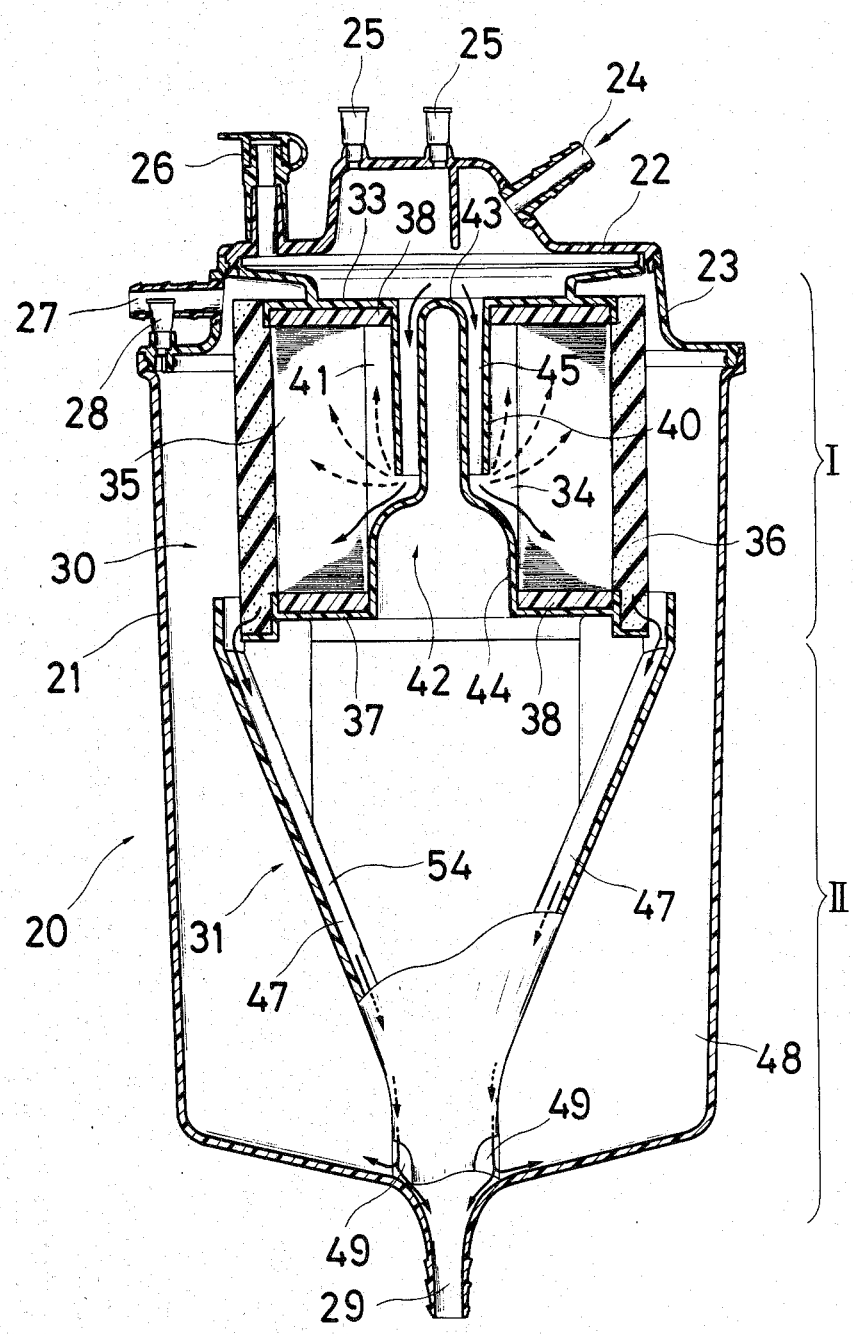
FIG. 4 is a sectional view of another embodiment of the blood reservoir of the invention in which the blood guide has a different construction.

The deflector 31 in the present invention that leads filtered and defoamed blood from filter/defoamer assembly 30 to the base of hollow housing 21 is illustrated by the embodiment just described. However, in other embodiments of this invention, housing 21 need not necessarily have a slanted base or a raised support. As shown in FIG. 4, blood that has been treated at filter/defoamer assembly 30 may also be led in the direction of the arrows by a deflector 31 that converges toward a blood outlet port 29 positioned at the center of the housing base. In this construction, it is desirable that a plurality of holes 49 be formed in the lower end of deflector 31 through which excess blood may enter a blood holding space 48. Since blood flows down over the inner surface of deflector 31, the color of the blood cannot be seen, unlike in conventional blood reservoirs where blood flows down over the outer surface. Then the level of the blood can be accurately observed, making it easy to measure the amount of blood in the reservoir. Making deflector 31 of opaque materials is even more effective.

The hollow housing 21, cylindrical wall 40, and distributor member 42 have all been described above as cylindrical, but these may be given any appropriate tubular shape, including elongated shapes of polygonal or irregular cross-section. It is equally clear that distributor member 42 may also be a solid.

The second feature of the present invention resides in the construction of filtration/defoaming section I in which a cylindrical barrier protects the upper portion of a filter from being wetted with blood such that bubbles or air in the blood may readily escape therethrough. The distributor member 42 which may be either hollow or solid functions to allow bubbles in the blood to float or emerge out on the blood surface before the blood reaches the filter, enabling efficient separation of bubbles.

According to one preferred embodiment of the present invention, the distributor member 42, cylindrical barrier 40, filter 35, and defoaming member 36 are concentrically arranged into an assembly, a blood channel is defined between distributor member 42 and cylindrical barrier 40, and a space 41 is defined between the cylindrical barrier 40 and filter 35 for allowing bubbles to separate from the blood. The usefulness of this construction was attested by the following experimentation.

A variety of filter assemblies were prepared as shown in FIGS. 5A through 5D. The filters used herein were the same in material, shape, and surface area. Pleated filters were used which were formed of nonwoven fabrics or meshes of synthetic fibers, for example, nylon, polyester, and polypropylene. The distributor member 42 and cylindrical barrier 40 were formed of a rigid plastic material as mentioned above. The defoamer member is omitted from these assemblies because the presence of a defoamer member about the filter renders inaccurate the observation of defoaming action. Bovine blood (aged one day after collection) was passed to these assemblies at a flow rate of 1,000 ml/min. to observe defoaming action and measure a pressure loss. The results are shown in Table 1.

TABLE 1

| Assembly | | Time, minute | | | | | | | |
|---|---|---|---|---|---|---|---|---|---|
| | | 5 | 10 | 15 | 20 | 25 | 30 | 40 | 50 | 60 |
| A | Pressure* | 7 | 9 | 12 | 13 | 15 | 16 | 17 | | |
| | Defoaming** | ◎ | ◎ | ◎ | ○ | ○ | △ | stop | | |
| B | Pressure | 20 | 24 | 35 | 50 | 63 | | | | |
| | Defoaming | ◎ | ○ | ▌ | X | stop | | | | |
| C | Pressure | 7 | 15 | 18 | 19 | 21 | 23 | 25 | 24 | 23 |
| | Defoaming | ◎ | ◎ | ◎ | ○ | ○ | △ | △ | △ | △ |
| D | Pressure | 2 | 3 | 5 | 8 | 8 | 11 | 11 | 10 | 8 |
| | Defoaming | ◎ | ◎ | ◎ | ◎ | ◎ | ◎ | ◎ | ◎ | ◎ |

Figure 5A:
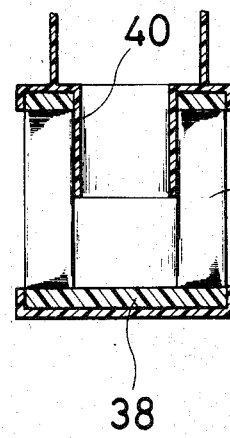
FIGS. 5A to 5D are cross-sectional views of different examples of the filter assembly used to examine the effectiveness of filter construction.
Figure 5B:
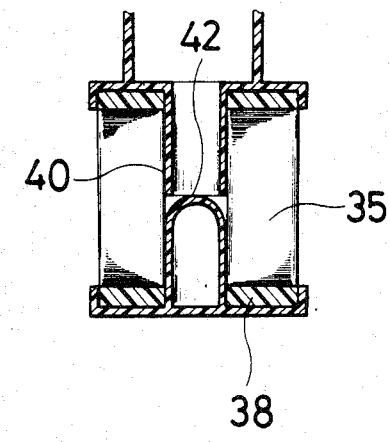
Figure 5C:
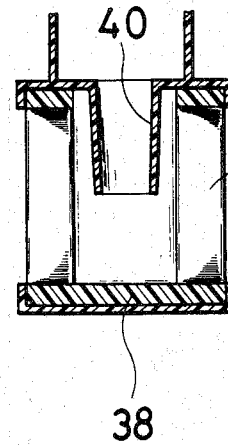
Figure 5D:
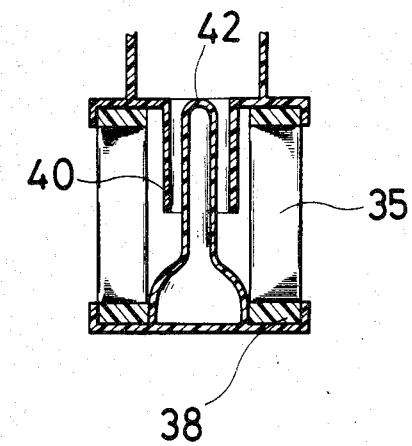

*Pressure loss in mmHg
**Symbols have the following meanings
◎ no bubble
○ some bubbles generated, but did not flow away
△ bubbles generated and flowed away
▌ noticeable bubbling
X the housing was full of bubbles Assembly A shown in FIG. 5A had the distributor member omitted. Bubbled blood flowed down directly onto lower adhesive layers 38 and bubbles were forced out of filter 35 by the blood. Assembly B shown in FIG. 5B had distributor member 42 terminating at the level of the lower open end of barrier 40 and thus in contact with the filter folds substantially up to that level. Assembly B thus had a relatively shorter length of filter effective to allow air to pass therethrough than assembly D shown in FIG. 5D. As a result, filter 35 of assembly B was more fast wetted to reduce the air permeable area. Assembly B exhibited inferior performance to assembly A. Assembly C shown in FIG. 5C had the distributor member omitted and cylindrical barrier 40 spaced from the filter folds. As compared with assemblies A and B, assembly C showed superior performance with acceptable pressure losses. Assembly D shown in Fig. 5D had cylindrical barrier 40 and distributor member 42 in a telescopic relationship. It exhibited the best performance. For assemblies C and D, it is believed that the presence of space 41 between barrier 40 and filter 35 prevents the upper portion of the filter from being wetted with blood and thus ensures smooth passage of air. In addition to space 41 between barrier 40 and filter 35, distributor member 42 is present in assembly D. Bubbled blood comes and flows down in continuous contact with distributor member 42. This continuous contact flow allows bubbles to emerge or float, facilitating the separation of bubbles from the blood.

Although a pleated filter was used in the above experiment and is described as being preferred in the disclosure, the filter which can be used herein is not restricted to pleated one. It will be understood that the advantage of providing a space between the cylindrical barrier and the filter becomes more outstanding when annular filters are applied.

Figure 7:
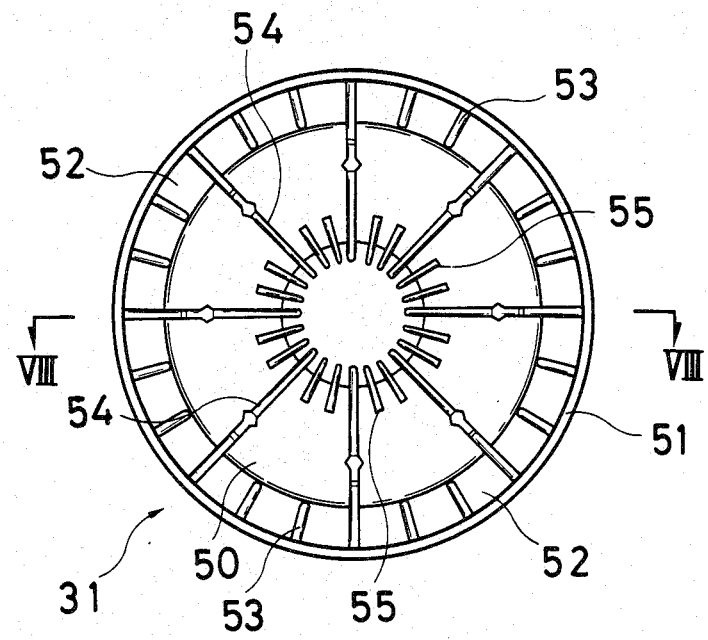
FIG. 7 is a plan view of a cone-shaped deflector used as the guide means in the blood reservoir.
Figure 8:
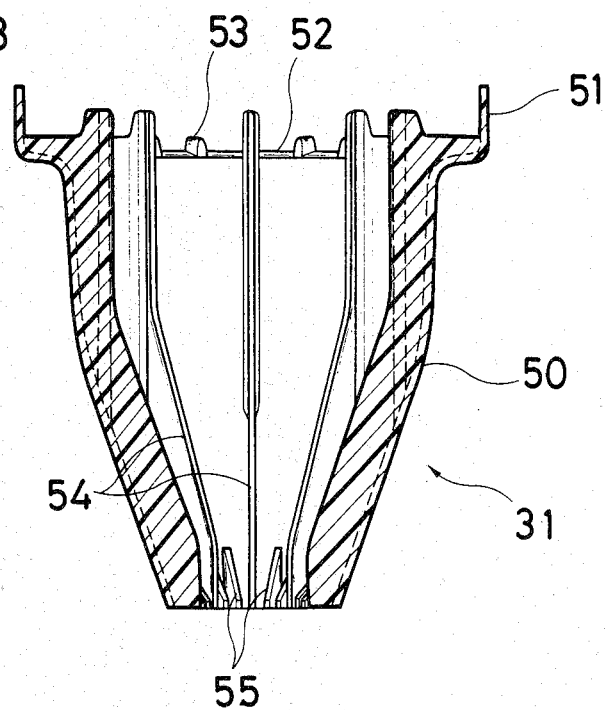
FIG. 8 is a vertical sectional view of the deflector taken along lines VIII—VIII in FIG. 7.

A further preferred embodiment of the blood reservoir according to the present invention is illustrated in FIGS. 6A, 7, and 8. Particularly, the guide means comprising the deflector 31 is illustrated in more detail. That is, there is illustrated the preferred deflector 31 which can lead filtered and defoamed blood from filter/defoamer assembly 30 to the base of housing 21 without reemerging bubbles therein particularly at the junctions between filter/defoamer assembly 30 and deflector 31 and between deflector 31 and raised support 32 on the housing base. Filter/defoamer assembly 30 at its lower circumferential edge delivers defoamed blood to deflector 31. This lower edge of filter/defoamer assembly 30 is hereinafter referred to as a delivery edge and provided by the outer periphery of tricot cover 46 in an exact sense.

As previously mentioned, deflector 31 is of a substantial cone shape having a divergent open end in engagement with the lower edge of filter/defoamer assembly 30 and a convergent open end in engagement with raised support 32 on the housing base. Deflector 31 has a convergent inner surface along which defoamed blood flows down.

As best shown in FIG. 8, deflector 31 comprises a substantially frustoconical barrel 50 which is provided at the upper end with a vertically and circumferentially extending flange 51 and a substantially horizontal, but slightly ramped shoulder 52. Flange 51 and shoulder 52 constitutes that portion of the deflector inner surface that receives blood emerging from the delivery edge of filter/defoamer assembly 30, particularly defoamer 36 through tricot cover 46. If blood drops from the delivery edge onto the receiving portion or shoulder 52 under gravity, then bubbles will be created again in the blood by such impact.

Figure 9:
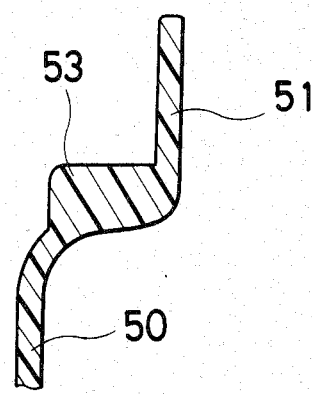
FIG. 9 is a cross section of a rib formed near the divergent end of the deflector.

To avoid bubble reemergence, the delivery edge of filter/defoamer assembly 30 is spaced from shoulder 52 on deflector 31 at a distance equal to or slightly less than the vertical dimension of a blood droplet hanging from the delivery edge. Then, upon transferring from the delivery edge of filter/defoamer assembly 30 to shoulder 52 on deflector 31, blood will not form a droplet. Blood is prevented from dripping down onto shoulder 52. However, if the distance between the delivery edge and shoulder 52 is too small, there remains only a narrow passage for blood, which can cause bubbling when a large volume of blood passes at a time. For this reason, said distance should be equal to or slightly less than the vertical dimention of a blood droplet. More preferably, shoulder 52 is provided with a plurality of radial ribs 53 which serve as part of the guide means and assist in leading blood from the delivery edge to the shoulder without dripping. Preferably at least three ribs 53 are equally spaced in a circumferential direction. The preferred configuration of rib 53 is shown in FIG. 9.

Preferably filter/defoamer assembly 31 is constructed such that defoamed blood emerges out at the outer circumferential edge of tricot cover 46. Tricot cover 46 at the center is forced upward by means of ribs 53 such that the lower circumferential edge of tricot cover provides a sharply configured edge.

With this arrangement, blood passes from the delivery edge of assembly 30 including defoamer 36 and tricot cover 46 to substantially horizontal shoulder 52 on deflector 31 without reemerging bubbles. It then flows down along the inner surface of convergent barrel 50 of deflector 31 under gravity. It finally reaches the lower or convergent end of barrel 50 and migrates to raised support 32 on the housing base.

Barrel 50 of deflector 31 is provided on the inner surface with a plurality of radial fins 54 to define a plurality of blood flow channels 47. Fins 54 extend the entire length of barrel 50. The provision of channels 47 serves to divide the blood into a plurality of streams to minimize the possible bubbling of blood. In addition to fins 54, barrel 50 is provided at the lower end with a plurality of radial sub-fins 55, preferably two or three equally spaced sub-fins per channel as illustrated in FIG. 7. These sub-fins divide each channel into a corresponding plurality of sub-channels, that is, divide each blood stream into smaller streams, thereby preventing the reemergence of bubbles due to flow pressure or the formation of a bubble membrane which can otherwise occur when blood passes between the lower end of deflector barrel 50 and raised support 32.

Figure 10:
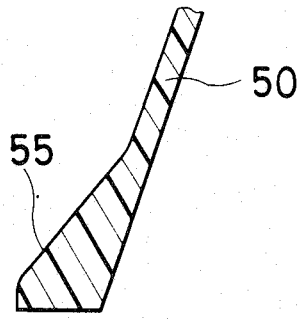
FIG. 10 is a cross section of a sub-fin formed at the convergent end of the deflector.

Again, provision must be made between the delivery end of deflector 31 and raised support 32 of the housing base such that blood is delivered from the deflector to the housing base smoothly without dripping or bubbling. Sub-fins 55 are preferably equally spaced in a circumferential direction at the lower end of barrel 50. The configuration and number of sub-fins 55 are such that the delivery opening of deflector barrel 50 may have a sufficient area to ensure smooth fast flow for even a volume of blood as great as 5 liters and the spacing between sub-fins is sufficient to prevent blood from forming a bubble membrane. The preferred configuration of sub-fin 55 is illustrated in FIG. 10. At least eight (8) sub-fins 55 are preferably formed. Test results show that less than eight sub-fins 55 are insufficient to provide uniform streams or to prevent microbubbles from occurring due to rupture of bubble membranes.

OPERATION

The filtration, defoaming, and blood collection functions during the use of the blood reservoir according to the present invention will now be described.

Figure 1:
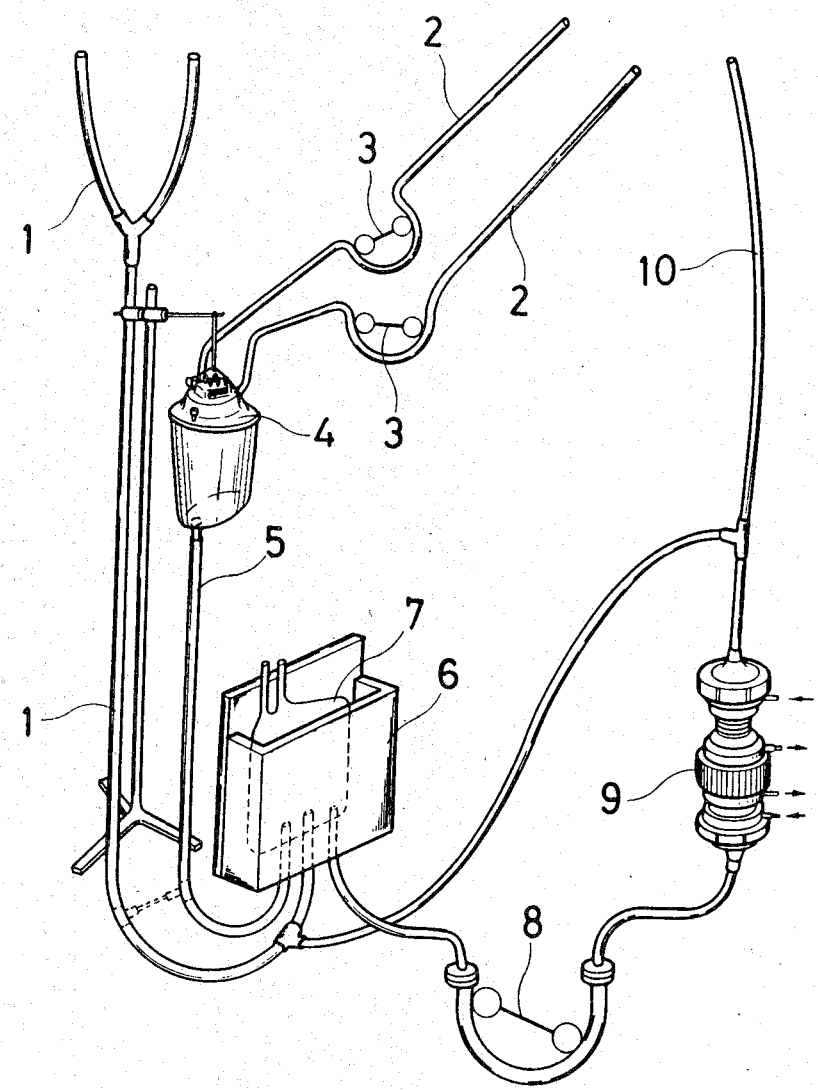
FIG. 1 is a perspective view of a typical oxygenator circuit.

The blood reservoir is used in a setup such as that shown in FIG. 1. Bubble-containing blood aspirated from the surgical field including the thoracic and cardiac cavities during open-heart surgery or other procedures passes through blood inlet port 24 and drops onto the round head of distributor member 42. The blood passes through the blood flow channel between upper portion 43 of distributor member 42 and barrier 40, flowing downward without direct contact with filter 35 until it reaches lower portion 44 of distributor member 42, where the first direct contact with filter 35 occurs. From the time the blood passes from the upper portion 43 of distributor member 42 until it comes into contact with filter 35 after passing over lower portion 44, the bubble-containing blood is contacted with these members over a sufficient surface area to separate more or less bubbles from the blood. The bubbles separated out collect in space 41 between filter 35 and barrier 40 so that they are not swept by the blood through the filter.

In FIGS. 3, 4 and 6A blood flow is represented by solid lines, and the flow of bubbles by broken lines. After being separated from the blood, the bubbles collect in space 41 and are defoamed as they pass through filter 35 with or without defoaming agent impregnated and defoamer 36. This air is discharged to the reservoir exterior through vent port 27. In this arrangemant, bubbles do not collect within cavity 34 of filter 35 or build up the pressure that would work together with the pressure of positive filtration to cause bubbles to spurt out together with the blood from filter 35.

Another improvement concerns the blood that collects within the cavity of filters used in conventional blood reservoirs. In blood reservoirs according to the present invention, the presence of distributor member 42 and the rapid, effective separation of blood and bubbles described above minimizes the amount of blood pooled in cavity 42. It is thus possible to accurately determine the amount of blood in the reservoir.

Filter 35 disposed about the periphery of distributor member 42 filters out foreign matter such as tissue and microaggregates present in the patient's blood or transfusing blood after the blood has been evenly distributed by distributor member 42 and bubbles effectively separated off to space 41 between distributor member 42 and barrier 40.

Blood that has been filtered or filtered and defoamed by filter 35 in this way is completely defoamed while passing through defoamer 36, and then oozes out of defoamer 36 and tricot cover 46. Blood then transfers from the delivery edge of filter/defoamer assembly 30 to horiontal shoulder 52 of deflector 31 without dripping. The smooth transfer of blood is ensured since tricot cover 46 at the center is forced upward by means of ribs 53 such that the lower circumferential edge of tricot cover provides a sharply configured edge. The blood that has reached shoulder 52 of deflector 31 without dripping then gently flows down under gravity in a plurality of streams along trough-like channels 47 defined by axial fins 54 on the deflector inner surface, and reaches the convergent open end of barrel 50 of deflector 31. The blood streams are further divided into smaller streams by means of sub-fins 55 at the convergent end of deflector 31. The arrangement of the deflector end and raised support 32 including the provision of sub-fins 55 allows blood to transfer from the deflector 31 to raised support 32 without reemerging bubbles because the formation of bubble membranes at the deflector end is prevented. Blood thus enters space 48 where it forms a swirling flow about raised support 32 on the sloped base of housing 21 and passes out through blood outlet port 29 and tubing 5 to venous reservoir 7 (see FIG. 1).

By positioning blood outlet port 29 near the periphery of the base of housing 21 rather than at the center, and providing it with a wide, smoothly curved, hemispherical shape, even a small amount of blood can, when necessary, be easily read out by means of a graduated scale marked on the outer wall of blood outlet port 29. Since the provision is made such that induces a swirling flow of blood at the base of housing 21 and ensures smooth flow through blood outlet port 29, blood gently flows in continuous contact with the base of housing 21, blood outlet port 29, and the walls of the tubing connected therewith. This prevents "air blocking", eliminating the danger of microbubbles passing into the patient's body via the venous reservoir.

Because the capacity of blood holding space 48 in blood collecting section II is 500 to 2500 ml, blood collected does not remain in continuous contact with filter 35 and defoamer 36, reducing the chances of complement activation, silicone extraction, and other problems. Moreover, this blood collecting capacity is entirely adequate even during emergency procedures.

The blood receiving and treating devices of the present invention have many advantages over conventional blood reservoirs. Some of these advantages are given below.

(1) The filtration/defoaming section is entirely separated from the blood collecting section. Because reservoir components such as the filter and defoamer do not remain constantly immersed in the collected blood, there is very little chance of complement activation, silicone extraction, or other problems arising.

(2) The cylindrical barrier and distributor member are disposed concentrically within the filter cavity, and a space is formed between the cylindrical barrier and the filter. This promotes separation of blood and bubbles and permits the separated bubbles to escape as air through that part of the filter protected from wetting by the barrier. As a result, unlike in conventional blood reservoirs, there is no bubble-induced rise in internal pressure that cooperates with the positive pressure of forced filtration to push the bubbles together with the blood out through the filter. (3) The delivery edge of the filter/defoamer assembly is spaced apart from the horizontal shoulder of the deflector at a distance equal to or slightly less than the vertical dimension of a blood droplet hanging from the delivery edge. Blood is thus passed from the filter/defoamer assembly to the deflector without dripping or bubbling. (4) The deflector is provided with fins on its entire inner surface and with sub-fins on its convergent open end to cause blood to flow in streams and finally in smaller streams. Blood is thus passed from the deflector end to the housing base without dripping or bubbling.

What is claimed is:

1. A device for receiving and treating blood, comprising
  a hollow housing having a top, a base, inlet means and an outlet, said inlet means being opened at the housing top for introducing blood into the housing and said outlet being opened at the housing base for discharging blood out of the housing,
  an upper filtration/defoaming section disposed in said housing for filtering and defoaming blood from said inlet means, said filtration/defoaming section including:
    a tubular filter,
    a tubular member defining a blood channel in communication with the blood inlet at the housing top and disposed inside said tubular filter to extend a part of the axial length of said tubular filter for protecting the upper portion of said tubular filter from being wetted with blood, said tubular member being spaced apart from said tubular filter to define a space for allowing bubbles to separate from the blood, and
    a defoaming member disposed about said tubular filter,
  a lower blood collecting section defined in said housing adjacent to its base for collecting blood, the blood in said collecting section discharging out of the housing through the outlet, and
  guide means extending between said filtration/defoaming section and the housing base and shaped to converge from said filtration/defoaming section toward the center of said housing base, said guide means including a convergent inner surface for continuously leading blood that has been filtered and defoamed in said filtration/defoaming section to the housing base along the inner surface without dripping.

2. The device according to claim 1 wherein said guide means comprises a deflector member extending from the lower edge of said filtration/defoaming section to the base of said housing.

3. The device according to claim 1 wherein said filtration/defoaming section is of cylindrical configuration, and said guide means comprises a cone-shaped deflector having a divergent open end in engagement with the lower edge of said filtration/defoaming section and a convergent open end in engagement with the base of said housing for fluid communication.

4. The device according to claim 3 wherein said guide means further comprises a plurality of fins formed on the inner surface of said cone-shaped deflector to define a corresponding plurality of blood flow channels.

5. The device according to claim 3 wherein said guide means further comprises a support protruding from the base of said housing and in engagement with the convergent open end of said cone-shaped deflector.

6. The device according to claim 1 wherein said housing is a substantially cylindrical elongated one.

7. The device according to claim 6 wherein the base of said housing is sloped in one direction.

8. The device according to claim 7 wherein the outlet is positioned at the lowest of the sloped base of said housing.

9. The device according to claim 6 wherein the base of said housing is sloped toward its center where the outlet is positioned.

10. The device according to claim 1 wherein said housing is a substantially cylindrical elongated one whose base is sloped toward its center where the outlet is positioned, said filtration/defoaming section is of cylindrical configuration, and said guide means comprises a cone-shaped member having a divergent open end in engagement with the lower edge of said filtration/defoaming section and a convergent open end in engagement with the base of said housing for fluid communication, the convergent end of said cone-shaped member being provided with at least one cut-out.

11. The device according to claim 1 wherein said blood collecting section has a capacity of about 500 to 2,500 ml.

12. The device according to claim 1, wherein the convergent inner surface of said guide means is smooth and continuous.

13. The device according to claim 1 wherein said filration/defoaming section further comprises
  means for distributing the blood coming from said blood inlet uniformly to the filter.

14. The device according to claim 13 wherein said distributing means is an elongated cylindrical member disposed inside said filter and extending through said tubular member in a telescopic manner.

15. The device according to claim 14 wherein said tubular member, tubular filter, defoaming member, and distributing member are concentrically arranged into an assembly.

16. The device according to claim 14 wherein said distributing member is of a tapered step structure having a lower portion of a large diameter in contact with the filter and an upper portion of a small diameter extending through the tubular member to define the blood channel therebetween.

17. The device according to claim 12 wherein said tubular member extends substantially one-half of the axial length of the filter.

18. The device according to claim 12 wherein said filter is pleated.

19. A device for receiving and treating blood comprising
a hollow housing having a top, a base, inlet means and an outlet, said inlet means being opened at the housing top for introducing blood into the housing and said outlet being opened at the housing base for discharging blood out of the housing,
an upper filtration/defoaming section in said housing,
a lower blood collecting section disposed in said housing vertically separate from said upper filtration/defoaming section, said blood collecting section being of a capacity such that blood collected therein does not remain in continuous contact with said filtration/defoaming section, and
guide means for continuously leading blood that has been filtered and defoamed in said filtration/defoaming section to the housing base without dripping,
said filtration/defoaming section including
a tubular filter,
a tubular member means defining a blood channel in communication with the blood inlet at the housing top and disposed inside said tubular filter to extend a part of the axial length of said tubular filter for protecting an upper portion of said tubular filter from being wetted with blood, said tubular member being spaced apart from said tubular filter to define a space for allowing bubbles to separate from the blood, and
a defoaming member disposed about said tubular filter.

20. The device according to claim 19 wherein said filtration/defoaming section includes a delivery extremity through which blood is delivered from said filtration/defoaming section to said guide means, and the distance between the delivery extremity and that portion of the inner surface of said guide means that receives blood from the delivery extremity is equal to or less than the vertical dimension of a blood droplet hanging from the delivery extremity.

21. The device according to claim 20 wherein said filtration/defoaming section is of cylindrical configuration, and said guide means comprises a cone-shaped deflector having a divergent open end in engagement with the lower edge of said filtration/defoaming section and a convergent open end in engagement with the base of said housing for fluid communication.

22. The device according to claim 21 wherein the delivery extremity is the lower edge of the circumference of said filtration/defoaming section.

23. The device according to claim 21 wherein the receiving portion is defined by a shoulder formed on the divergent end portion of said deflector.

24. The device according to claim 23 wherein the delivery extremity of said filtration/defoaming section is spaced apart from the shoulder of the deflector by means of a plurality of ribs formed on the shoulder in engagement with the lower edge of said filtration/defoaming section.

25. The device according to claim 24 wherein the ribs are circumferentially equally spaced.

26. The device according to claim 21 wherein said guide means further comprises means for defining a plurality of blood flow channels on the inner surface of said cone-shaped deflector.

27. The device according to claim 26 wherein said channel defining means comprises a plurality of radial fins formed on the inner surface of said deflector.

28. The device according to claim 27 wherein said fins are circumferentialy equally space and extend the entire length of said deflector.

29. The device according to claim 27 wherein said channel defining means further comprises a plurality of radial sub-fins formed on the convergent end portion of the deflector inner surface to divide each of the blood flow channels into narrow sub-channels.

30. A device for receiving and treating blood comprising
a holllow housing having a top, a base, inlet means and an outlet, said inlet means being opened at the housing top for introducing blood into the housing and said outlet being opened at the housing base for discharging blood out of the housing, and
a filtration/defoaming section disposed in said housing to receive bubbled blood through said inlet means and including:
a tubular filter,
a tubular member defining a blood channel in fluid communication with the blood inlet at the housing top and disposed inside said tubular filter to extend a part of the axial length of said tubular filter for protecting an upper portion of said tubular filter from being wetted with blood, said tubular member being spaced apart from said tubular filter to define a space for allowing bubbles to separate from the blood, and
a defoaming member disposed about said tubular filter.

31. The device according to claim 30 wherein said filtration/defoaming section further comprises
means for distributing the blood coming from said inlet means uniformly to the filter.

32. The device according to claim 31 wherein said distributing means is an elongated cylindrical member disposed inside said filter and extending through said tubular member in a telescopic manner.

33. The device according to claim 32 wherein said tubular member, tubular filter, defoaming member, and distributing member are concentrically arranged into an assembly.

34. The device according to claim 32 wherein said distributing member is of a tapered step structure having a lower portion of a large diameter in contact with the filter and an upper portion of a small diameter extending through the tubular member to define the blood channel therebetween.

35. The device according to claim 30 wherein said tubular member extends substantially one-half of the axial length of the filter.

36. The device according to claim 30 wherein said filter is pleated.

37. The device according to claim 33 wherein said filtration/defoaming section further comprises a tricot cover enclosing the defoaming member.

38. The device according to claim 1 wherein said housing is provided at the top with a cover assembly comprising first and second covers which are mated for rotation with each other.

39. The device according to claim 30 wherein said housing is provided at the top with a cover assembly comprising first and second covers which are mated for rotation with each other.

* * * * *

UNITED STATES PATENT AND TRADEMARK OFFICE
CERTIFICATE OF CORRECTION

PATENT NO. : 4,664,682

DATED : May 12, 1987

INVENTOR(S) : Takashi MONZEN

It is certified that error appears in the above-identified patent and that said Letters Patent is hereby corrected as shown below:

COLUMN 9, line 27, (TABLE 1), "°15" should read --15--;

COLUMN 16, line 32, (Claim 30), after "member", insert --means--.

Signed and Sealed this

Third Day of May, 1988

*Attest:*

DONALD J. QUIGG

*Attesting Officer*      *Commissioner of Patents and Trademarks*

UNITED STATES PATENT AND TRADEMARK OFFICE
CERTIFICATE OF CORRECTION

PATENT NO. : 4,664,682

DATED : May 12, 1987

INVENTOR(S) : Takashi MONZEN

It is certified that error appears in the above-identified patent and that said Letters Patent is hereby corrected as shown below:

COLUMN 15, line 7 (Claim 17), "12" should read --1--;

line 10 (Claim 18), "12" should read --1--.

Signed and Sealed this

Fourth Day of October, 1988

*Attest:*

DONALD J. QUIGG

*Attesting Officer*     *Commissioner of Patents and Trademarks*